Figure 1:
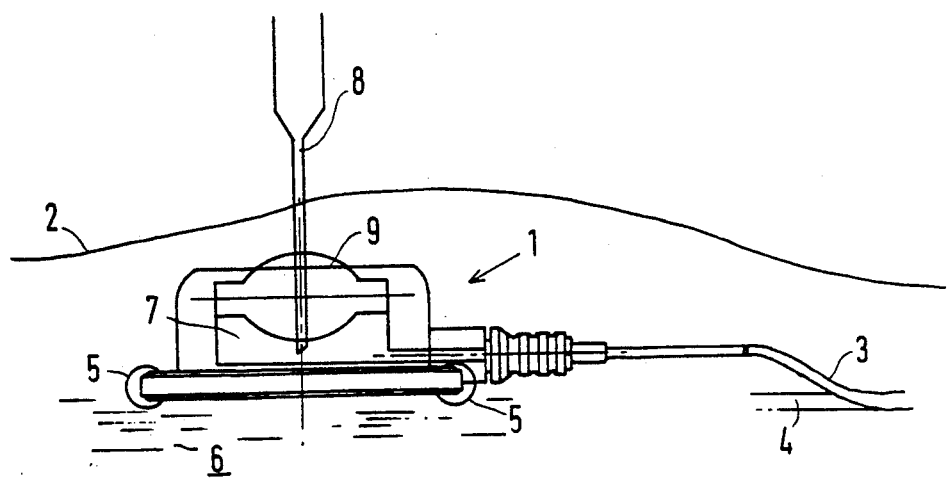

United States Patent [19]

Dijkstra et al.

[11] Patent Number: 5,026,344
[45] Date of Patent: Jun. 25, 1991

[54] IMPLANTABLE INJECTION CHAMBER DEVICE

[76] Inventors: Klaas Dijkstra, Wolddijk 80, 9784 TE Noordwolde; Frans P. Boersma, Brabantselaan 26, 9501 AC Stadskanaal, both of Netherlands

[21] Appl. No.: 452,789

[22] Filed: Dec. 19, 1989

[30] Foreign Application Priority Data

Oct. 19, 1988 [NL] Netherlands ............... 8802577

[51] Int. Cl.⁵ .................... A61M 11/00; A61K 9/22
[52] U.S. Cl. .................... 604/93; 604/891.1; 604/48
[58] Field of Search ............... 604/891.1, 21, 27, 47, 604/48, 51–53, 93; 623/11, 66

[56] References Cited

U.S. PATENT DOCUMENTS

| | | | |
|---|---|---|---|
| 4,398,910 | 8/1983 | Blake et al. | 604/93 |
| 4,652,255 | 3/1987 | Martinez | 604/27 |
| 4,781,680 | 11/1988 | Redmond et al. | 604/93 |
| 4,955,861 | 9/1990 | Enegren et al. | 604/93 |

FOREIGN PATENT DOCUMENTS

| | | |
|---|---|---|
| 0091773 | 10/1983 | European Pat. Off. |
| 0258580 | 3/1988 | European Pat. Off. |
| 2612784 | 9/1988 | France |
| 891392 | 3/1962 | United Kingdom |
| 2020385 | 11/1979 | United Kingdom |

Primary Examiner—Alan Cannon
Attorney, Agent, or Firm—Peter L. Michaelson

[57] ABSTRACT

An implantable injection chamber device comprising a housing which encloses an injection chamber and has at least one wall that can be pierced with a hollow needle, and a bore provided in a wall of the chamber, there being further provided connecting means for connecting a catheter to the bore, and in which the connecting means comprise a tube of pliable material which is connected to the bore and in operation extends through a bore in a first member of the connecting means, at least a part of said first member surrounding the tube relatively tightly and said part being provided with a plurality of radially disposed longitudinal grooves; and a second member of the connecting means is provided, which in operation surrounds the part of the first member that is provided with longitudinal grooves and is capable of pressing inwardly the parts of the first member between the longitudinal grooves.

16 Claims, 2 Drawing Sheets ably be made of metal, the parts 18 of the member 15 will actually be able to locally cause a deformation of the tube 10 so as to press it firmly against the catheter 3. Thus the catheter is locked.

IMPLANTABLE INJECTION CHAMBER DEVICE

The invention relates to an implantable injection chamber device comprising a housing which encloses an injection chamber and has at least one wall that can be pierced with a hollow needle, and a bore provided in a wall of the chamber, there being further provided connecting means for connecting a catheter to the bore.

A similar injection chamber device is known per se from practice and serves to facilitate the prolonged or frequent administration of medicines. The injection chamber device is intended to be implanted close under the patient's skin, with the pierceable wall turned towards the skin. By means of a needle, which is introduced through the skin and the special pierceable wall, a medicine is injected into the injection chamber. From the injection chamber the medicine can be supplied vascularly or derospinally or to a body cavity via a catheter. The pierceable wall is a silicone membrane, which closes again after removal of the needle. The needle may for instance be a hypodermic needle with a syringe for intermittent administration or, for instance, a needle connected to an infusion device (a so-called drip) or a pump for continuous administration.

Since the injection chamber device is implanted subcutaneously it is of great importance that the connection with the catheter can reliably and easily be made. According to the prior art to make the connection between the injection chamber and a catheter, a metal tube is used which is connected to the injection chamber device, links up with the bore in the chamber wall, and is connected to a catheter by means of a metal or synthetic plastics clamp which is pinched fast.

A drawback of the device according to the prior art is that squeezing with pincers will cause a deformation of the metal or synthetic plastics clamp that is not entirely within one's control, so that one cannot always be sure that the connection has actually been made in the way intended. Furthermore, the catheter and/or the tube may be damaged when the clamp is pinched tight. Further, the outlet tube of the chamber may perforate the catheter during the subcutaneous implantation.

The present invention aims to overcome the drawbacks outlined above and generally to provide an injection chamber device which can safely and simply be connected to a catheter.

To this effect an implantable injection chamber device of the kind described above is characterized according to the present invention in that the connecting means comprise a tube of pliable material which is connected to the bore and in operation extends through a bore in a first member of the connecting means, at least a part of said first member surrounding the tube relatively tightly and said part being provided with a plurality of radially distributed longitudinal grooves; and that a second member of the connecting means is provided, which in operation surrounds the part of the first member that is provided with longitudinal grooves and is capable of pressing inwardly the parts of the first member between the longitudinal grooves.

Figure 2:
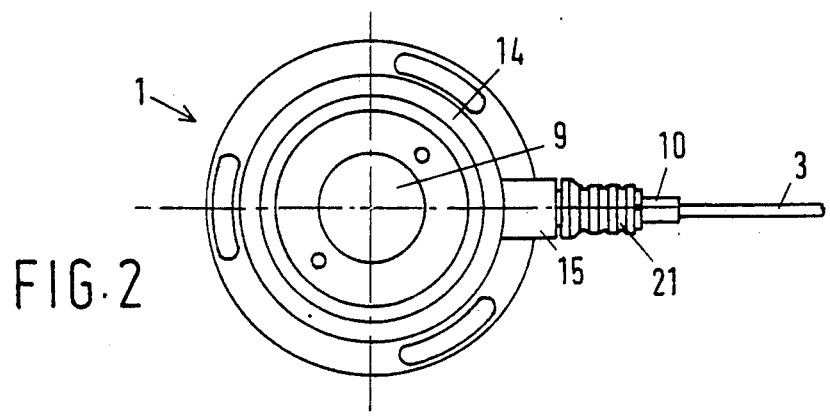
Figure 4:
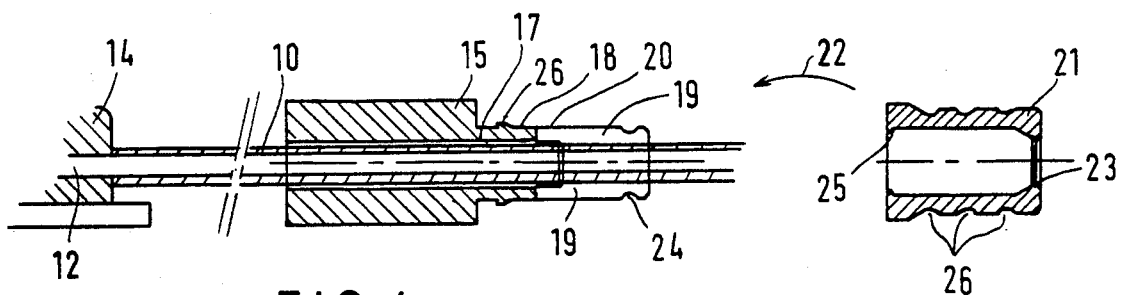
Figure 5:
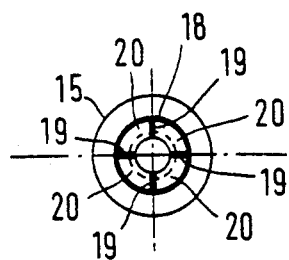
Figure 3:
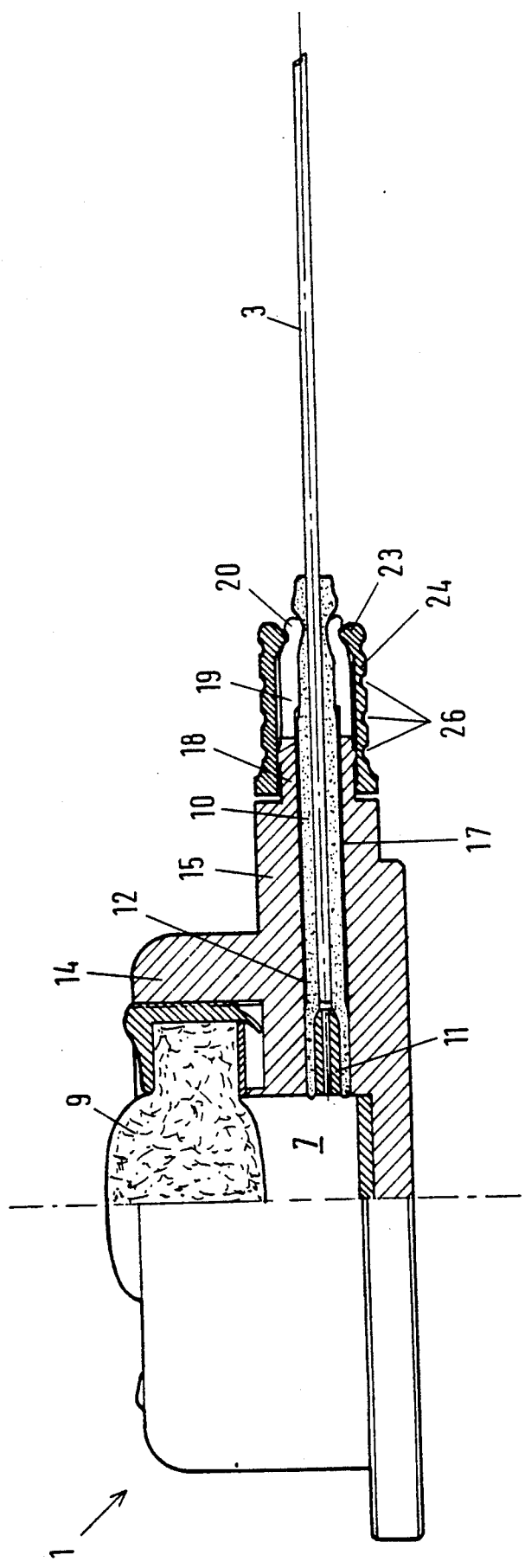

The invention will now be further described, by way of example, with reference to the accompanying drawings, in which FIG. 1 schematically illustrates in what way an injection chamber device is applied;

FIG. 2 schematically shows a top plan view of an example of a device according to the invention;

FIG. 3 schematically shows a part-sectional view of an embodiment of a device according to the invention;

FIG. 4 schematically shows a cross-sectional exploded view of an example of a device according to the invention; and FIG. 5 shows in end view one of the members of the connecting means of FIG. 4.

FIG. 1 illustrates schematically in what way an injection chamber device, also referred to as drip gate, is applied. The injection chamber device 1 is implanted under a patient's skin 2 and via a catheter 3 fluids are supplied vascularly, derospinally or to a body cavity. The injection chamber device 1 may be secured to a layer of muscular tissue 6 by means of a plurality of sutures 5. The injection chamber device comprises a chamber 7, which in operation is filled with the fluid to be administered to the patient. To that effect there is provided a wall 9 of, for instance, silicone rubber, which wall can be pierced by means of a hollow needle 8, for instance that of a syringe.

An example of an injection chamber device according to the invention is schematically shown in top plan view in FIG. 2 and partly in cross-section in FIG. 3. FIGS. 2 and 3 show that the catheter has been slid into a tube 10. The tube 10 is made of pliable material and in turn secured in a bore 12 through the wall of the injection chamber 1. As shown in FIG. 3, a hollow plug 11 may be used for this purpose, which plug is slid into the tube 11 from the side of chamber 7, the wall of the tube thus being wedged between the plug 11 and the wall of the bore 12. The tube 10, which may, for instance, be made of silicone rubber, extends from the chamber 7 through the wall 14 of the device and through a first member 15 of the connecting means. In the embodiment shown in FIGS. 2 and 3 the member 15 is an integral part of the chamber wall 14. As is shown in FIG. 4 the member 15 may also be a separate member, which may optionally be disposed at some distance from the chamber wall, as is also shown in FIG. 4.

The member 15 is provided with a longitudinal bore through which the tube 10 extends. At least a part 18 of the longitudinal bore 17, which part is at an end of the member 15, tightly surrounds the tube 10. As shown in FIG. 4, this part may advantageously have a relatively small wall thickness in relation to the rest of the member 15 and is further provided with a plurality of longitudinal slots 19. As shown in FIG. 5, the embodiment shown is provided with four longitudinal slots 19.

By providing the longitudinal slots, in fact four cylindrically arranged resilient tongues 20 are created, which to some extent can be bent towards each other to bring a radial compressive force to bear on the tube 10.

By means of the tongues 20, therefore, the tube can be locally constricted to some extent, thus holding down the catheter 3 it contains.

To move the tongues 20 inwardly a second member 21 is provided. The member is a tubular sliding sleeve and can be fitted so tightly over the part 18 of the member 15, as is indicated in FIG. 4 by an arrow 22, that the tongues 20 are squeezed against and into the wall of the tube 10.

To this effect the sliding sleeve 21 could, for instance, have an internal wall that is tapered at least in part. In the embodiment shown the sliding sleeve 21 has an internal annular shoulder 23, which can snap into an annular circumferential groove 24 of the part 18 of the member 15, but has an internal diameter that is slightly smaller than that of the circumferential groove when the tongues are in the inoperative position. If the sleeve is secured in the clamped position in a different manner, the circumferential groove need not unconditionally be provided.

The sliding sleeve may advantageously be provided with a second annular shoulder 25, which in operation engages behind a shoulder provided beyond the tongues 20 or in a groove provided in the first member beyond the tongues 20.

FIG. 4 shows such a shoulder at 26. The shoulder 26 is preferably disposed in such a way that it permits the sleeve to be shifted over part 18 between a clamping position (shown in FIG. 3) and an uncoupling position without the connection between the first and the second members being broken.

In the uncoupling position the tongues 20 are not squeezed and the catheter can be shifted in the tube 10 or be removed from it.

The sleeve, therefore, can already be mounted on the first member during manufacture, which reduces the risk of the sleeve being lost.

In the embodiment shown the sleeve is further provided with a plurality of circumferential grooves 26 which facilitate handling the sleeve.

It is noted that after reading the above various modifications of the embodiments described will readily occur to a person skilled in the art. Reference has already been made to the possibility of optionally forming the first member as an integral part of the chamber wall 14. A further possibility is to use a threaded sleeve instead of a sliding sleeve.

Shifting the sleeve between the clamping position and the uncoupling position is then effected by rotating the sleeve relatively to the part 18 in the manner of a nut. To this effect the sleeve may be internally threaded to cooperate with screwthread on the part 18 and the sleeve may be provided with a narrower part Capable of squeezing the tongues.

It is also possible to use a so-called bayonet joint, where the sleeve has a few inner projections, which in the clamping position fit into a recess of the part 18. To shift the sleeve from the uncoupling position to the clamping position it must first be shifted linearly and then turned. During this turning movement the sleeve may be moved further up the part 18 if the inner projections are moved along ascending shoulders on the part 18.

Further it is needless to say that instead of 4, a different number of tongues may be used.

The shoulders 23 and 25 may optionally comprise a plurality of annularly disposed projections.

These and similar modifications are considered to fall within the scope of the invention.

What we claim is:

1. An implantable injection chamber device comprising a housing which encloses an injection chamber and has at least one wall that can be pierced with a hollow needle, and a bore provided in a wall of the chamber, there being further provided connecting means for connecting a catheter to the bore, characterized in that the connecting means comprise a tube of pliable material which is connected to the bore and in operation extends through a bore in a first member of the connecting means, at least a part of said first member surrounding the tube relatively tightly and said part being provided with a plurality of radially disposed longitudinal grooves; and that a second member of the connecting means is provided, which in operation surrounds the part of the first member that is provided with longitudinal grooves and is capable of pressing inwardly the parts of the first member between the longitudinal grooves.

2. An implantable injection chamber device according to claim 1, characterized in that said longitudinal grooves of said first member extend from one end thereof to form resilient tongues between said longitudinal grooves.

3. An implantable injection chamber device according to claim 2, characterized in that said second member is a sleeve in operation surrounding said tongues and which presses said tongues inwardly.

4. An implantable injection chamber device according to claim 3, characterized in that said sleeve is internally tapered.

5. An implantable injection device according to claim 3, characterized in that the sleeve comprises first internal annular shoulder means.

6. An implantable injection chamber device according to claim 5, characterized in that the first member comprises an annular groove provided near the tongues, said groove in operation seating the shoulder of the sleeve.

7. An implantable injection chamber device according to claim 3, characterized in that the sleeve is a sliding sleeve.

8. An implantable injection chamber device according to claim 3, characterized in that the sleeve is a threaded sleeve.

9. An implantable injection chamber device according to claim 3, characterized in that the sleeve has second internal shoulder means, which in operation engage behind a corresponding shoulder of the first member.

10. An implantable injection chamber device according to claim 9, characterized in that the second internal shoulder means of the sleeve and the corresponding shoulder of the first member permit the sleeve to be displaced between a clamping position and an uncoupling position without the shoulders passing each other.

11. An implantable injection chamber device according to claim 1, characterized in that the first member forms an integral part of the housing.

12. An implantable injection chamber device according to claim 1, characterized in that the tube is clamped tight in the bore in the chamber wall by means of a bored plug.

13. An implantable injection chamber device according to claim 1, characterized in that the second member is provided with external grooves and/or ribs.

14. An implantable injection chamber device according to claim 1, characterized in that the second member can be coupled to the first member by means of a bayonet joint.

15. An implantable injection chamber device according to claim 14, characterized in that the sleeve is provided with one or more internal projections, which cooperate with ascending shoulders in the first member.

16. A connecting arrangement for connecting an injection chamber with a catheter, which comprises first and second cooperating members according to claim 1.

* * * * *